(12) United States Patent
Leathe et al.

(10) Patent No.: US 10,473,552 B1
(45) Date of Patent: Nov. 12, 2019

(54) TEST ARTIFACT FOR NON-DESTRUCTIVE EVALUATION

(71) Applicant: National Technology & Engineering Solutions of Sandia, LLC, Albuquerque, NM (US)

(72) Inventors: Nicholas Leathe, Albuquerque, NM (US); Nicolas Argibay, Albuquerque, NM (US)

(73) Assignee: National Technology & Engineering Solutions of Sandia, LLC, Albuquerque, NM (US)

(*) Notice: Subject to any disclaimer, the term of this patent is extended or adjusted under 35 U.S.C. 154(b) by 106 days.

(21) Appl. No.: 15/950,905

(22) Filed: Apr. 11, 2018

Related U.S. Application Data

(60) Provisional application No. 62/485,252, filed on Apr. 13, 2017.

(51) Int. Cl.
| | |
|---|---|
| *G01M 7/00* | (2006.01) |
| *B29C 64/386* | (2017.01) |
| *G01N 27/20* | (2006.01) |
| *B33Y 40/00* | (2015.01) |
| *B33Y 70/00* | (2015.01) |
| *B29C 64/153* | (2017.01) |
| *B22F 3/105* | (2006.01) |
| *B33Y 50/02* | (2015.01) |

(52) U.S. Cl.
CPC .............. *G01M 7/00* (2013.01); *B29C 64/386* (2017.08); *G01N 27/20* (2013.01); *B22F 2003/1057* (2013.01); *B29C 64/153* (2017.08); *B33Y 40/00* (2014.12); *B33Y 50/02* (2014.12); *B33Y 70/00* (2014.12)

(58) Field of Classification Search
CPC ....... G01M 7/00; G01N 27/20; B29C 64/386; B33Y 40/00
See application file for complete search history.

(56) References Cited

U.S. PATENT DOCUMENTS

| | | | | |
|---|---|---|---|---|
| 2017/0254740 A1* | 9/2017 | Carpick | .................. | G01Q 60/26 |
| 2018/0231581 A1* | 8/2018 | Dharmasena | .......... | G01Q 70/10 |

OTHER PUBLICATIONS

Advertisement/information for Anton-Paar Nano Tribometer (NTR3) at www.anton-paar.com, accessed Apr. 11, 2018 (https://www.anton-paar.com/us-en/products/details/nano-tribometer-ntr3/).

* cited by examiner

*Primary Examiner* — David Z Huang
(74) *Attorney, Agent, or Firm* — Samantha Updegraff

(57) ABSTRACT

The present invention relates to an additively manufactured (AM), monolithic, multi-axis linear flexural cantilever test artifact. The artifact is monolithic in that is it one continuous part with no assembly. The artifact can be non-destructively evaluated and includes a support frame, cantilevers, and a mount.

20 Claims, 9 Drawing Sheets

TEST ARTIFACT FOR NON-DESTRUCTIVE EVALUATION

RELATED APPLICATIONS

This application claims priority to U.S. Provisional Application No. 62/485,252, filed on Apr. 13, 2017, and entitled NON-DESTRUCTIVELY EVALUATED TEST ARTIFACT, the entirety of which is incorporated herein by reference

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD OF THE INVENTION

The present invention relates to test artifacts for material characterization and/or characterization of mechanical properties and more specifically relates to non-destructively characterizing material and mechanical properties of test artifacts.

BACKGROUND OF THE INVENTION

Material property characterization for additively manufactured structures has mimicked wrought material characterization through the utilization of standard test artifacts such as the American Society for Testing and Materials (ASTM) tensile bars. To determine material properties from this process, the test artifacts are routinely destructively tested. In the characterization of additively manufactured materials, traditional test artifacts developed for the characterization of homogeneous wrought materials and not for additively manufactured materials have been heavily utilized. These test artifacts, maintained by agencies such as ASTM or the American Society of Mechanical Engineers (ASME), are destructively tested to extract mechanical properties such as Young's modulus or yield strength. These traditional test artifacts work well for wrought material, as it has not only been extensively characterized and is well understood, but it is also homogeneous through an ingot. Additively manufactured materials however, behave differently from conventional wrought alloys and thus require different test artifacts and techniques for characterization.

Accordingly, there is a need for a test artifact for use in non-destructively characterizing mechanical properties and specifically address functional mechanical properties driven from design expectations for material performance. There is also a need for test artifacts to permit characterization of multiple properties and be an endorsement that a build was "acceptable". Embodiments of the present invention meet the needs stated above. The test artifact of the present invention is designed for testing to determine mechanical properties using non-destructive evaluation techniques for the opportunity to use one test artifact for multiple test setups. This is important for additive material characterization for multiple reasons.

The test artifact of the present invention can characterize multiple mechanical and material properties, such as, for example, Young's modulus or shear modulus, harmonic response, surface roughness, density, hardness testing, flex to failure (ultimate/yield strength), and cycle flexure to evaluate fatigue properties. Additionally, the test artifact and corresponding characterizations can significantly reduce the uncertainty associated with measurements. The test artifact can be an endorsement that a build process and any post processing procedures were acceptable, possibly eliminating the need for current extensive post build part evaluation.

SUMMARY OF THE INVENTION

One embodiment of the present invention is a test artifact. The test artifact of this embodiment has a support frame, a first cantilever section disposed on the support frame, the first cantilever section having two cantilevers, and a second cantilever section disposed on the support frame and substantially parallel to the first cantilever section, the second cantilever section having two cantilevers. The test artifact also has a support beam connecting the first cantilever section to the second cantilever section, an end portion connecting a cantilever from the first cantilever section to a cantilever from the second cantilever section and disposed on ends of the corresponding cantilevers opposite the support beam, a protrusion disposed on the end portion, and a mounting portion attached to the support frame. The mounting portion can optionally include one or more fixturing stubs and an opening. The cantilevers of this embodiment can be substantially the same thickness or can vary in thickness. The thickness of each respective cantilever can remain constant, and the thickness of a first cantilever can vary from the thickness of a second cantilever. The cantilevers can also vary in height along a length of a corresponding cantilever. The height of each cantilever can be greater at an end adjacent to the support beam than at a corresponding end adjacent to the end portion. This embodiment can optionally include a center portion disposed between the first cantilever section and the second cantilever section. The center portion extends from the end portion. The mounting portion of this embodiment can be substantially perpendicular to the cantilevers or substantially parallel to the cantilevers. This embodiment can also optionally include a third cantilever section and a fourth cantilever section. The third cantilever section is preferably adjacent to the first cantilever section and the fourth cantilever section is preferably adjacent to the second cantilever section. The support frame may be c-shaped. The test artifact can be one continuous part with no assembly.

Another embodiment of the present invention is a test artifact that has a support frame, a first cantilever section attached to the support frame, the first cantilever section having at least one first support cantilever and at least one first load cantilever, a second cantilever section attached to the support frame and substantially parallel to the first cantilever section, the second cantilever section having at least one second support cantilever and at least one second load cantilever. A support beam is attached to the at least one first support cantilever, the at least one first load cantilever, the at least one second support cantilever, and the at least one second load cantilever. A load portion is attached to the at least one first load cantilever and the at least one second load cantilever at ends of the corresponding load cantilevers opposite the support beam. A protrusion is attached to the end portion. A mounting portion is attached to the support frame. In this embodiment, the at least one first support cantilever includes two first support cantilevers and the at least one second support cantilever includes two second support cantilevers. The at least one first load cantilever can optionally include two first load cantilevers and the at least one second load cantilever can include two second load cantilevers. The test artifact of this embodiment can have the following cantilevers, two first support cantilevers, two first load cantilevers, two second support cantilevers, and two second load cantilevers.

Other features and advantages of the invention will be apparent from the following description and the claims.

DETAILED DESCRIPTION OF THE INVENTION

Figure 1A:
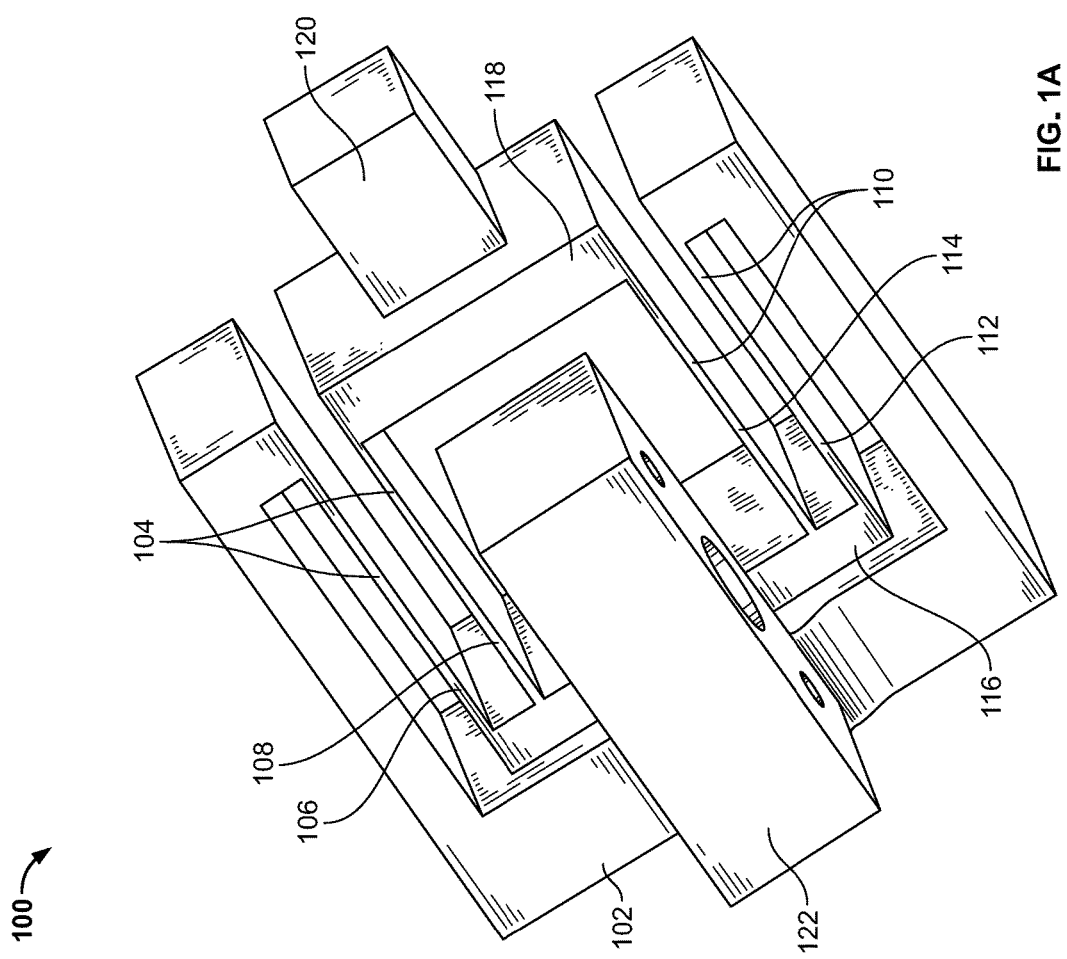
FIGS. 1A-1B are drawings that show perspective views of an embodiment of a test artifact of the present invention.

The ability to non-destructively evaluate a test artifact is important to gain an understanding of the behavior and changes a material undergoes as it is exposed to different environments. In wrought materials, statistical distributions of material properties are assumed as there is little variance throughout the billet of material. With additive manufacturing, this cannot be assumed for parts coming off the same build plate. These early indications imply that there are variances between builds, between additive manufacturing machines, and between regions within the same build. These variances, coupled with destructive evaluation techniques, inhibit the profound understanding of material changes through these environments. Specifically, an understanding of materials at extreme temperatures and their change from room temperature environments can be important for product qualification. Non-destructive techniques enable test artifacts to be evaluated multiple times, before, after, or during exposure to varying environments allowing for a complete profile of material behavior.

Non-destructive techniques also lead to better data, and a higher confidence in the measured results. This is accomplished with modal testing techniques, as the two parameters tested are typically highly accurate: time and mass. For example, in a conventional tensile bar test, there is an uncertainty associated with the applied load and the geometry of the artifact. However, with a modal technique, mass and time are the only variables and can be measured to extreme accuracy if required. This technique with an embodiment of the present invention additionally enables multi-axis material property characterization to capture inhomogeneity in printed material using axially coupled analyses. This is a marked improvement over tensile bars, which provide single axis characterization data. An embodiment of the test artifact of the present invention can be designed specifically for additive manufacturing characterization. A test artifact can be an endorsement that a build process and any post processing procedures were acceptable, possibly eliminating the need for current extensive post build part evaluation.

An embodiment of the present invention is a multi-axis linear flexural cantilever test artifact. The artifact is preferably a continuous part requiring no assembly for test and characterization, and deflects in a linear fashion so that there is only translation and no rotation in the geometry. This deflection in a linear fashion enables a simplified modal analysis that can be used to determine structure-property information. Rotation may complicate the analysis and make it impractical to implement. The test artifact of the present embodiment also lends itself to multiple material types, such as plastic, ceramic, or metal, and additive manufacturing processes, such as powder bed fusion, extrusion, or Laser Engineered Net Shape. The test artifact enables multiple tests through a series of environments for material assurance in additive manufacturing.

Figure 1B:
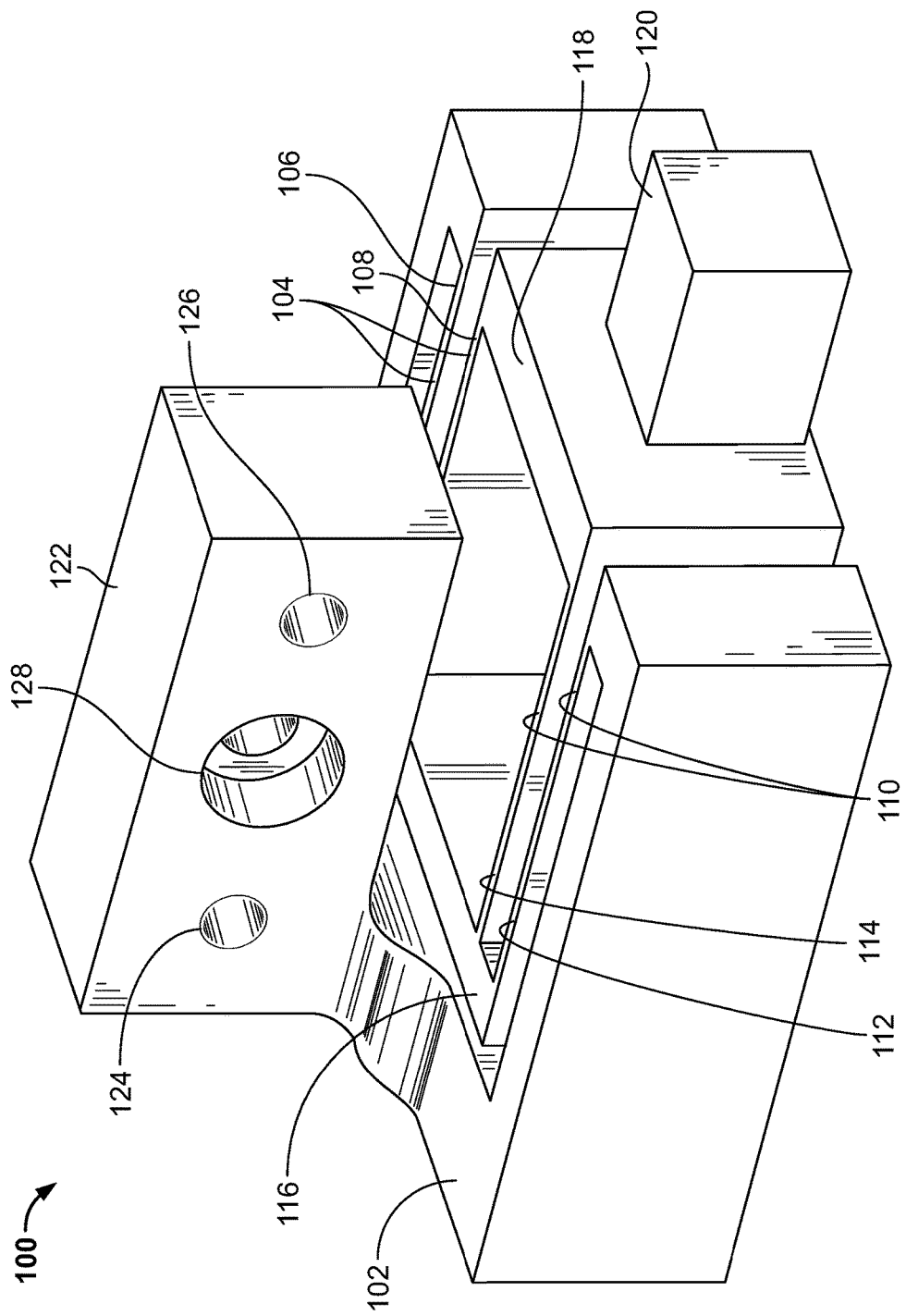

Referring to FIGS. 1A and 1B, test artifact 100 has support frame 102, first cantilever section 104 attached to support frame 102. First cantilever section 104 has at least one first support cantilever 106 and at least one first load cantilever 108. Second cantilever section 110 is attached to support frame 102 and is preferably substantially parallel to first cantilever section 104. Second cantilever section 110 has at least one second support cantilever 112 and at least one second load cantilever 114. Support beam 116 is attached to first support cantilever 106, first load cantilever 108, second support cantilever 112, and second load cantilever 114. Load portion 118 is attached to the at least one first load cantilever 108 and the at least one second load cantilever 114 at the ends of the corresponding load cantilevers opposite support beam 116. Protrusion 120 is attached to load portion 118. Mounting portion 122 is attached to support frame 102. In one embodiment, first support cantilever 106 has at least two first support cantilevers and second support cantilever 112 has at least two second support cantilevers. In addition, first load cantilever 108 can have at least two first load cantilevers and second load cantilever 114 can have at least two second load cantilevers.

Support frame 102 may be c-shaped with cantilevers 106, 108, 112, and 114 disposed within the c-shape of support frame 102. Protrusion 120 provides a measurement surface for recording the displacement, velocity, and acceleration of the cantilever structure. Mounting portion 122 has fixturing stubs 124 and 126 as well as opening 128 (see FIG. 1B). Fixturing stubs 124 and 126 are used for alignment purposes. Pins can be inserted into stubs 124 and 126 for alignment of test artifact 100 in a testing apparatus. These pins inserted into stubs 124 and 126 prevent rotation around opening 128. Opening 128 can accept a fastener for mounting artifact 100 on a test apparatus for evaluating test artifact 100. The secure mounting between the test artifact and the test apparatus preferably provides a consistent evaluation environment. Mounting portion 122 can extend above and substantially parallel to cantilever sections 104 and 110. Cantilevers 106, 108, 112, and 114 are preferably thin walled structures that can have varying thicknesses for bulk properties. For example, the thickness of each of the cantilevers 106, 108, 112, and 114 can vary, and/or thicknesses of one or more of cantilevers 106, 108, 112, and 114 can vary from one end of a cantilever to the other end (i.e., from support beam 116 to load portion 118). In this instance, a cantilever can have a thickness at one end of the cantilever (for example, a thickness at support beam 116) and a different thickness at the other end of the cantilever (load portion 118), either decreasing or increasing in thickness. Thicknesses of both types can range from about 0.5 mm to about 2.5 mm. Cantilevers 106, 108, 112, and 114 can each have different thicknesses within the same test artifact or can all have the same thickness. Cantilevers 106, 108, 112, and 114 can also each have different heights within the same test artifact or can all have the same heights. In addition, cantilevers 106, 108, 112, and 114 can have varying heights from one end of the cantilever to the other end of the same cantilever. In this instance, a cantilever can have a height at one end of the cantilever and a different height at the other end of the cantilever, either decreasing or increasing in height. Cantilevers 106, 108, 112, and 114 can also each have different lengths within the same test artifact or can all have the same lengths.

Figure 2A:
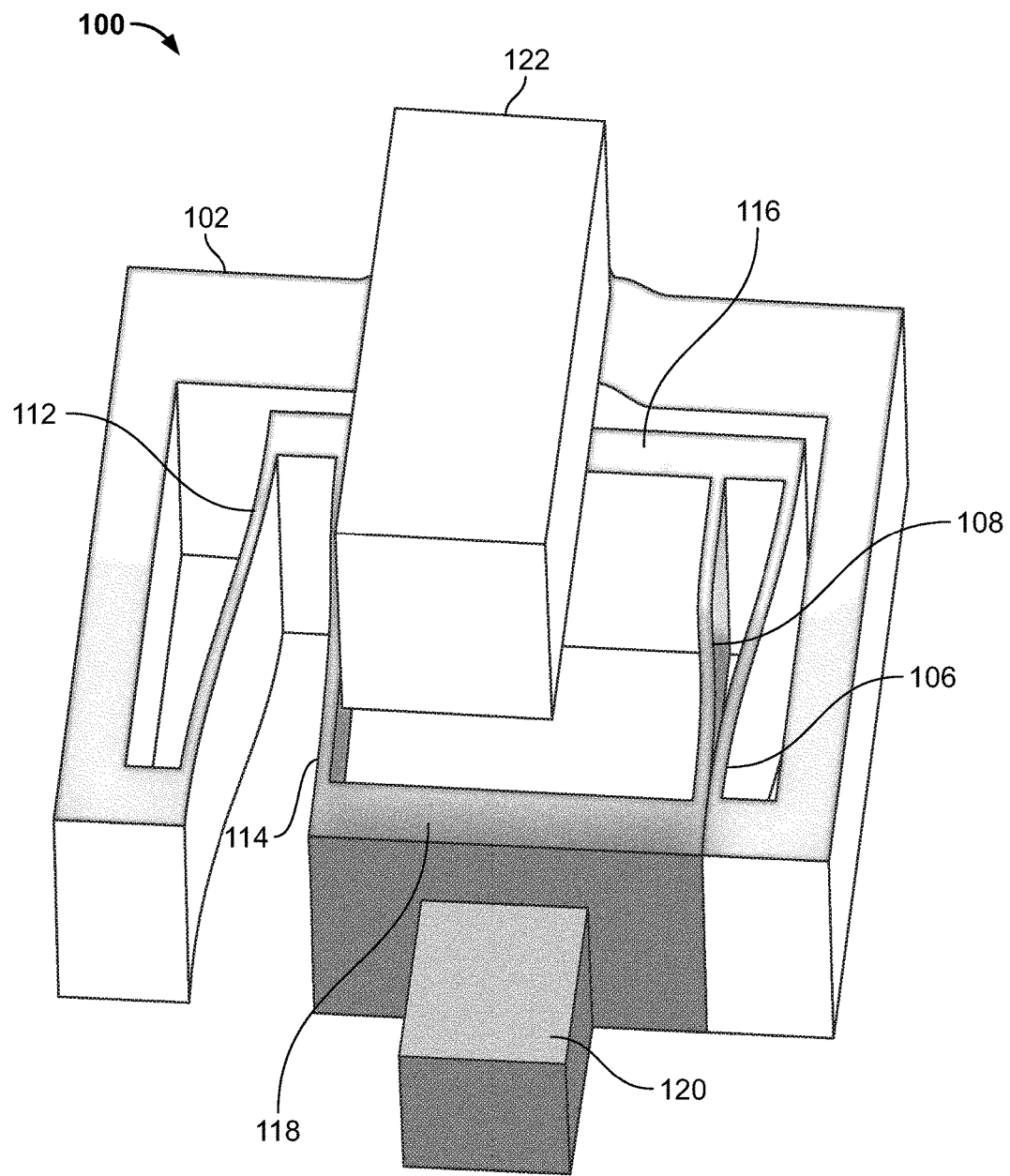
FIGS. 2A-2B show modal analyses performed on test artifacts.
Figure 2B:
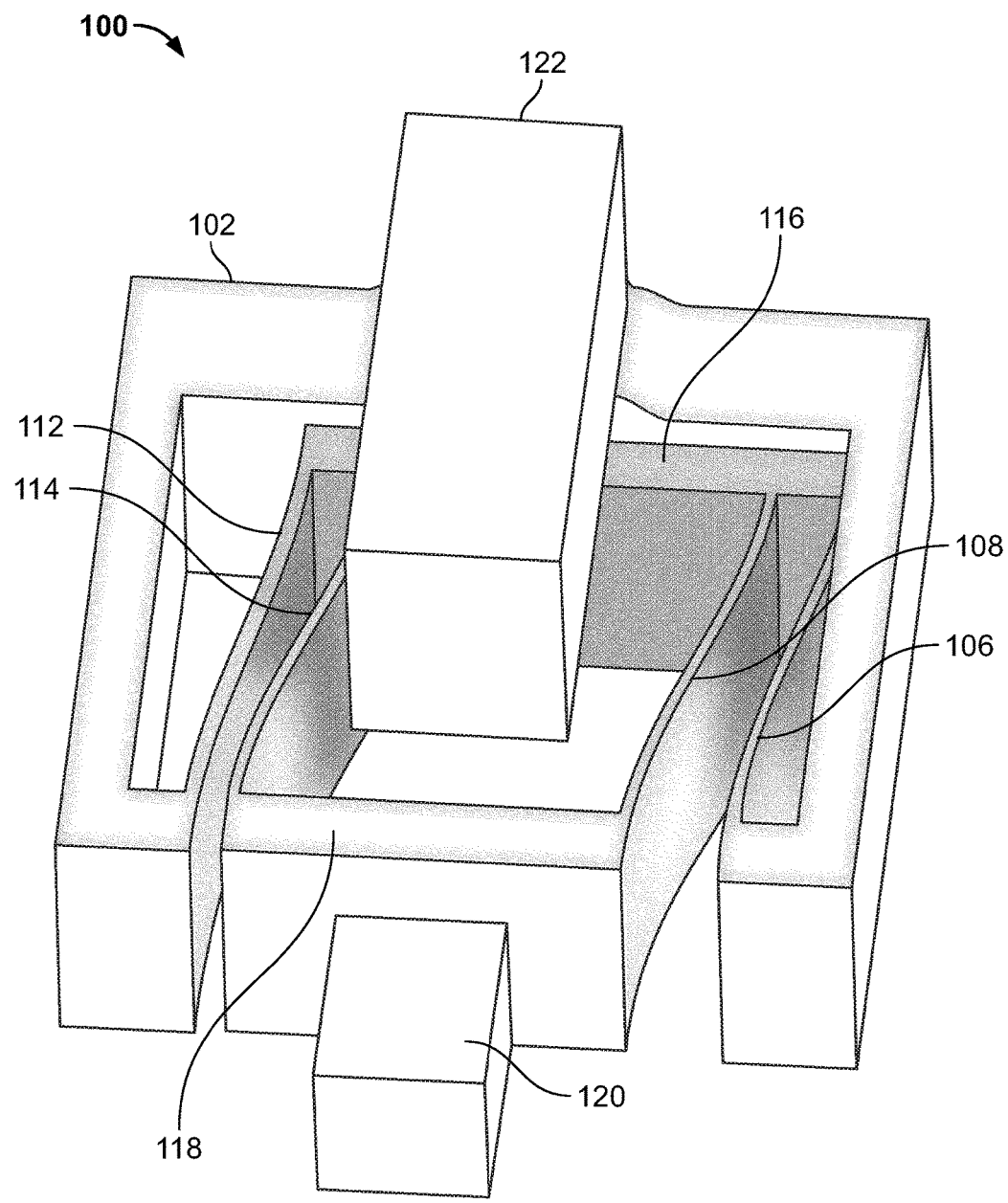

Referring to FIGS. 2A and 2B, test artifact 100 shows different harmonic (modal) responses. The stippled surface shading represents a scaled displacement. FIGS. 2A and 2B depict the motion of protrusion 120. In the first two natural frequency responses of the test artifact, the motion of protrusion 120 is along one axis, substantially parallel to one of the protrusion faces. This enables the use of a one-dimensional measurement technique to record and detect the movement of the protrusion.

Figure 3:
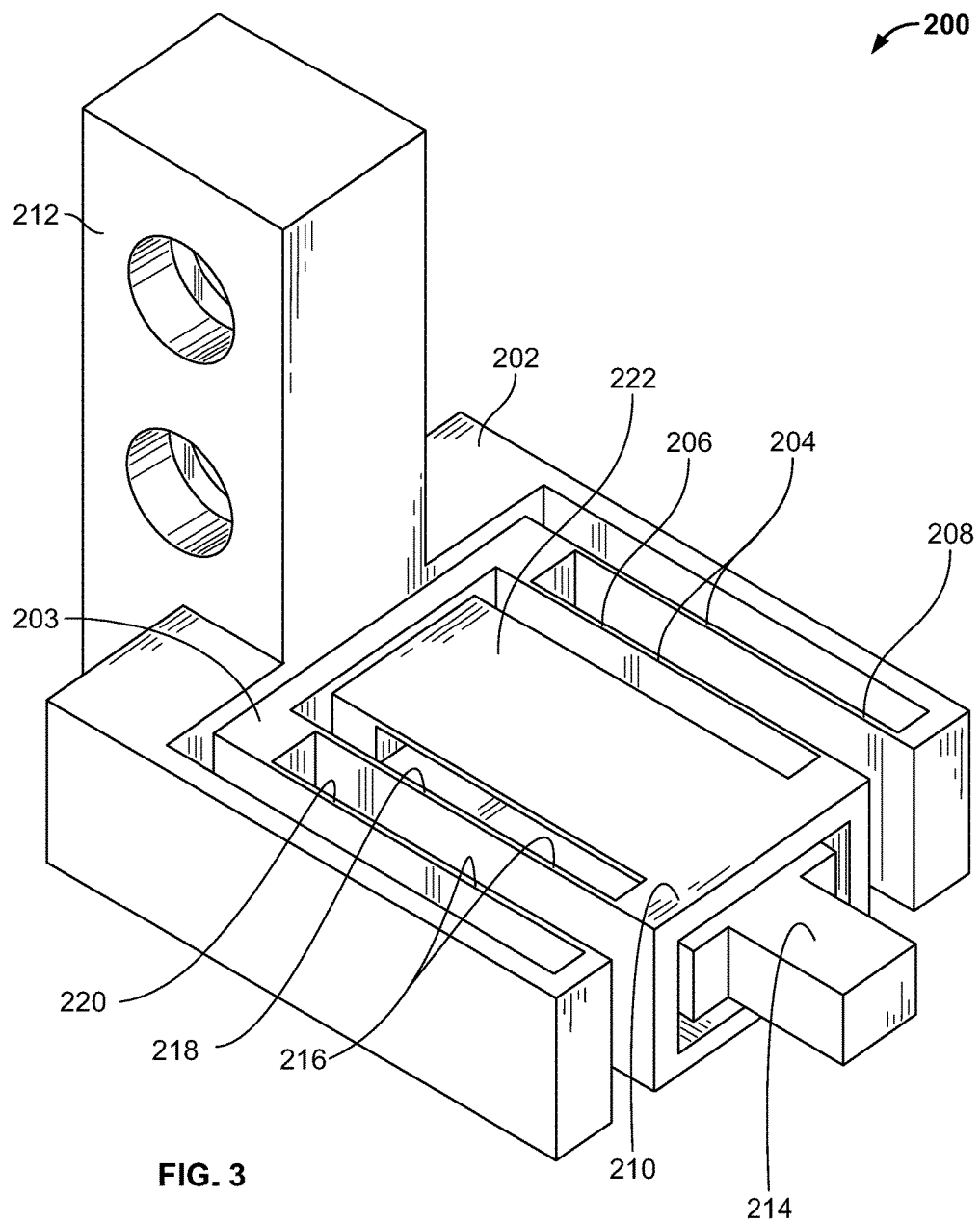
FIG. 3 is a drawing illustrating a perspective view of another embodiment of a test artifact of the present invention.
Figure 4:
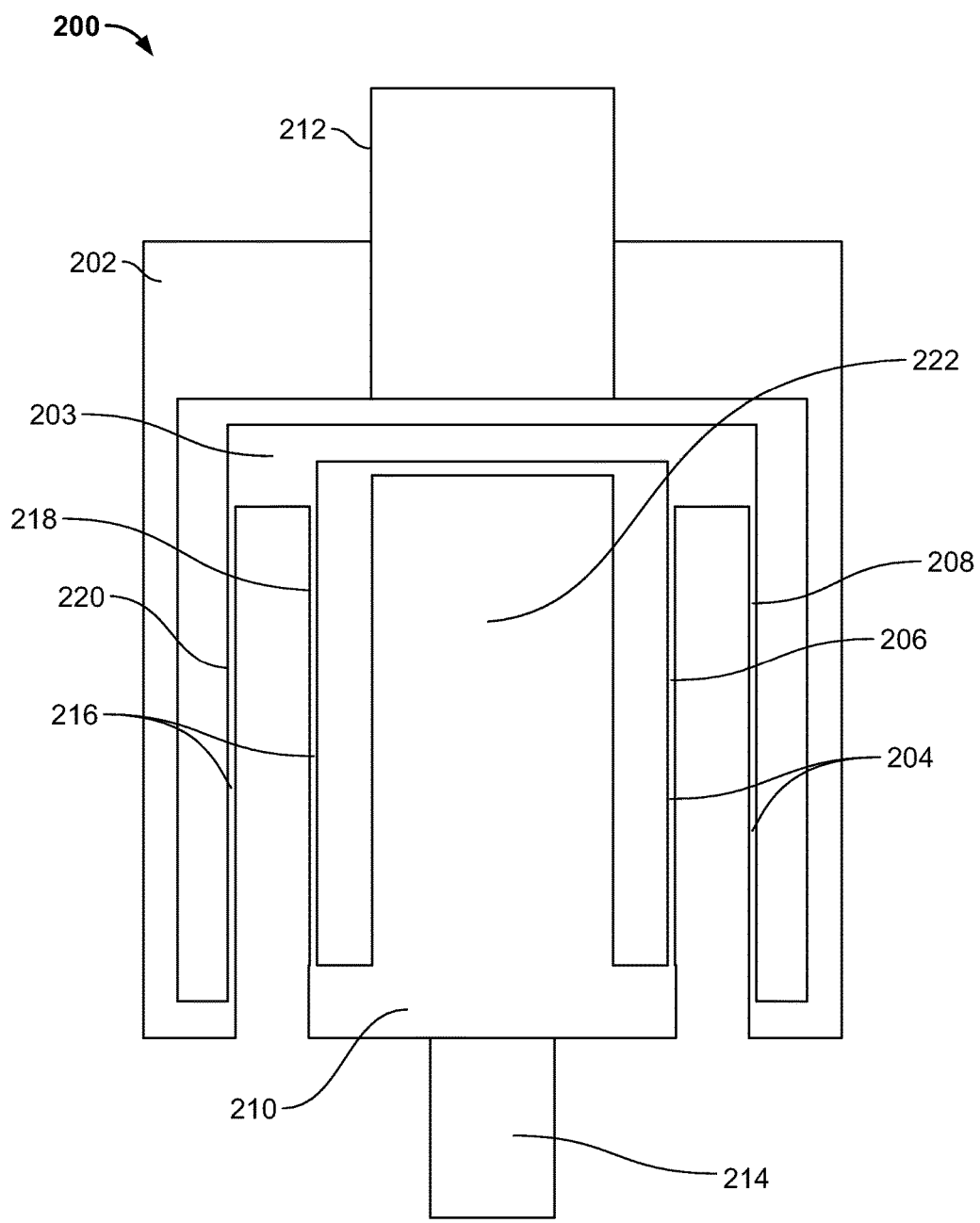
FIG. 4 is a drawing illustrating a top view of an embodiment of the present invention.
Figure 5:
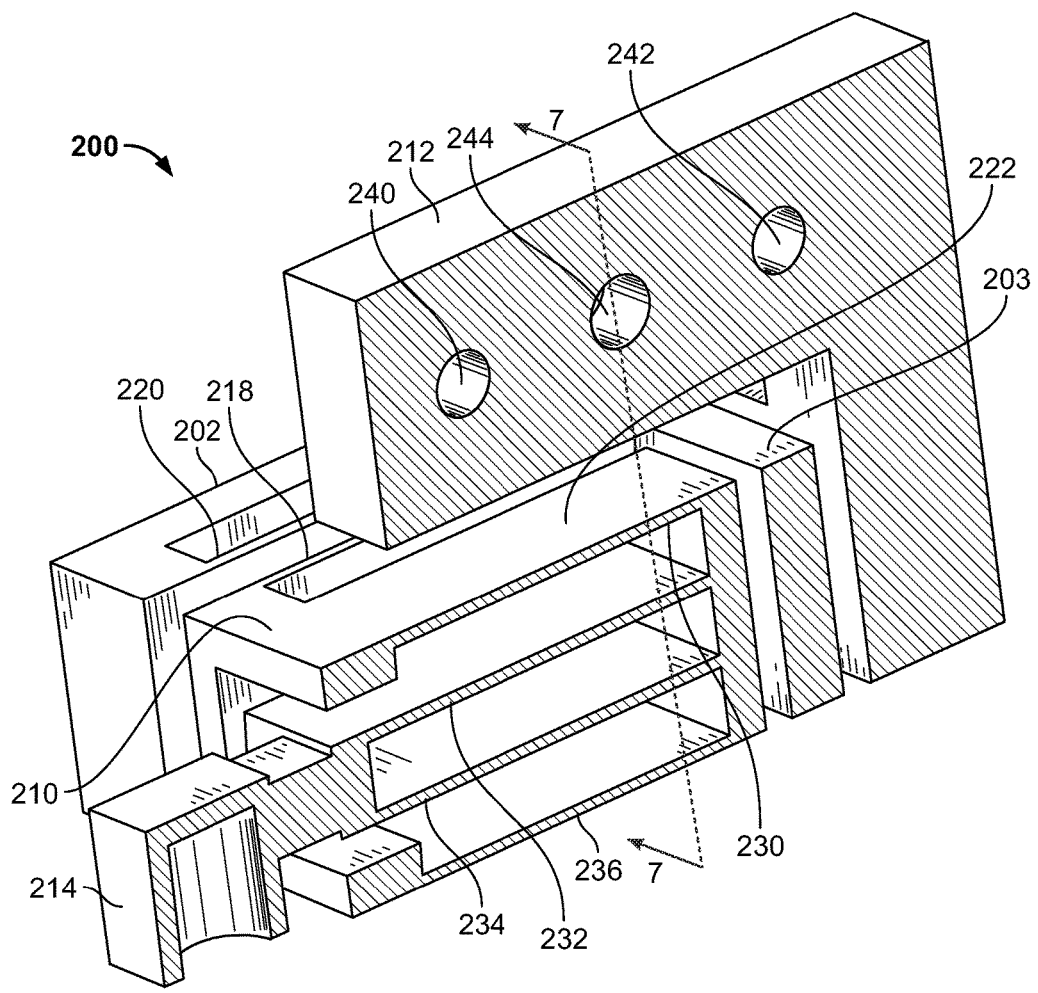
FIG. 5 is a drawing illustrating a cross-section perspective view of an embodiment of the present invention.
Figure 6:
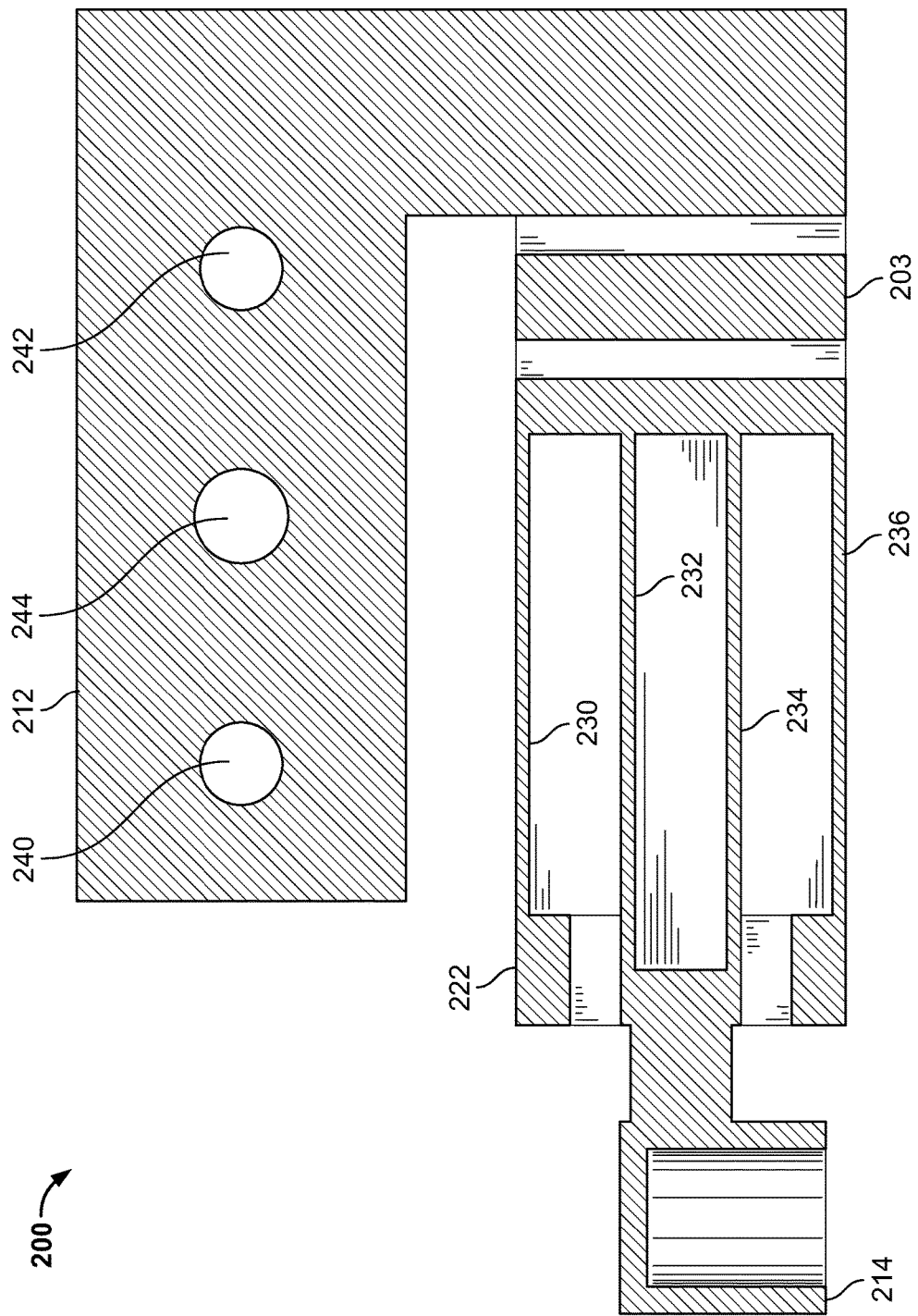
FIG. 6 is a drawing illustrating a cross-section side view of an embodiment of the present invention.
Figure 7:
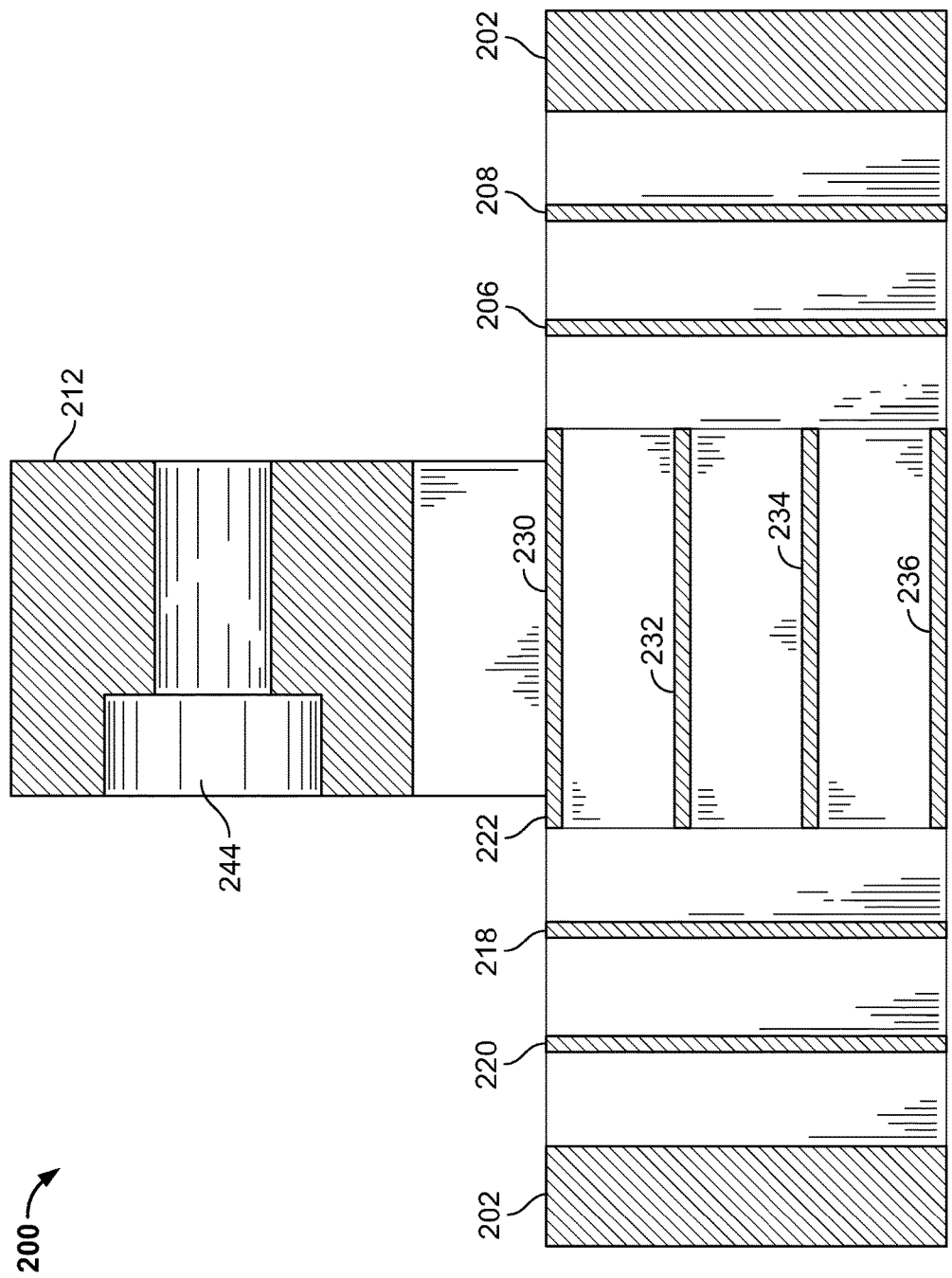
FIG. 7 is a drawing illustrating a cross-section front view of an embodiment of the present invention.

Referring to FIGS. 3-4, test artifact 200 includes center portion 222 disposed between cantilever sections 204 and 216. In this embodiment, mounting portion 212 is substantially perpendicular to support frame 202 and cantilever sections 204 and 216. However, mounting portion 212 can also be substantially parallel to cantilever sections 204 and 216 (see FIGS. 5-7). Protrusion 214 protrudes from end portion 210. Cantilevers 206, 208, 218, and 220 extend out from support beam 203, preferably in a substantially perpendicular direction. Center portion 222 preferably has cantilevers that are substantially orthogonal to cantilevers 206, 208, 218, and 220. Referring to FIGS. 5-7, cantilevers 230, 232, 234, and 236 are substantially perpendicular to cantilevers 206, 208, 218, and 220 and can be used for increased characterization of material and mechanical properties. Cantilevers 206, 208, 218, 220, 230, 232, 234, and 236 are preferably thin walled structures that can have varying thicknesses for bulk properties. For example, the thickness of each of the cantilevers' thin walls can vary, and thicknesses of one or more of cantilevers 206, 208, 218, 220, 230, 232, 234, and 236 can vary from one end of a cantilever to the other end. In this instance, a cantilever can have a wall thickness at one end of the cantilever and a different wall thickness at the other end of the cantilever, either decreasing or increasing in thickness. Thicknesses of both types can range from about 0.5 mm to about 2.5 mm. Cantilevers 206, 208, 218, 220, 230, 232, 234, and 236 can each have different wall thicknesses within the same test artifact or can all have the same wall thickness. Cantilevers 206, 208, 218, and 220 can also each have different heights within the same test artifact or can all have the same heights. In addition, cantilevers 206, 208, 218, and 220 can have varying heights from one end of the cantilever to the other end of the same cantilever. In this instance, a cantilever can have a height at one end of the cantilever and a different height at the other end of the cantilever, either decreasing or increasing in height. Cantilevers 230, 232, 234, and 236 can each have different widths within the same test artifact or can all have the same heights. In addition, cantilevers 230, 232, 234, and 236 can have varying widths from one end of the cantilever to the other end of the same cantilever. In this instance, a cantilever can have a width at one end of the cantilever and a different width at the other end of the cantilever, either decreasing or increasing in width. Cantilevers 206, 208, 218, 220, 230, 232, 234, and 236 can also each have different lengths within the same test artifact or can all have the same lengths.

Referring to FIGS. 5-6, mounting portion 212 has fixturing stubs 240 and 242 as well as opening 244. Fixturing stubs 240 and 242 are used for alignment purposes. Pins can be inserted into stubs 240 and 242 for alignment of test artifact 200 in a testing apparatus. These pins inserted into stubs 240 and 242 can prevent rotation around opening 244 (see also FIG. 7). Opening 244 can accept a fastener for mounting artifact 200 on a test apparatus for evaluating test artifact 200.

In another embodiment of the present invention, a test artifact can include three or more cantilever sections. Test artifact 200 includes one or more flat surfaces that can be used for profilometry, the geometry of test artifact 200 enables it to be easy to gauge for geometric dimensioning and tolerancing (GD&T). GD&T is a system used to define acceptable tolerances on part drawings. In this essence, the geometry of the test artifact is simple to gauge for dimensional accuracy of the part since it is a 2.5-dimensional structure. It can easily fit into a fixture to verify that the fabrication of the part fits within a certain tolerance range. There are no post processing requirements when using test artifact 200. The cantilevers of a test artifact can be used as a spring system for detecting natural response of the test artifact. The cantilever structure offers redundancy in ensuring a more accurate physical response, as each of the individual beams has an independent harmonic response. The frequency of the beams is proportional to the square root of the beam stiffness divided by its mass $$\left(f \alpha \sqrt{\frac{k}{m}}\right).$$

One embodiment of the present invention is an additively manufactured (AM), monolithic, multi-axis linear flexural cantilever test artifact. The artifact is monolithic in that it is one continuous part with no assembly. The artifact deflects in a linear fashion, i.e. translation but no rotation. This is achieved using moment-cancelling geometries. The linear flexural characteristic enables the kind of simplified vibration (modal) analysis that can be used to determine structure-property information. The artifact can vary in size. For example, an artifact can be as small as about 1 cm×1 cm×1 cm, and there is no constraint on how large the artifact can be and still function (e.g., about 20 cm×20 cm×20 cm), but there may be motivation for it to be as small as possible for practical reasons.

The test artifacts can be used for non-destructive modal analysis. The analysis can include, but is not limited to imparting an impulse to the cantilevers of the test artifact, preferably one axis at a time, and using sensors (e.g. capacitance probes, laser Doppler vibrometer, interferometers, accelerometers, optical high-speed video) to measure time-dependent evolution of position. Analysis of the time versus position data allows for a determination of damping coefficient, stiffness, shear modulus, and deviations from nominal response due to microstructural defects. The simplifications enabled by the geometry of the test artifact allow for correlation of the derived parameters (i.e. stiffness, damping coefficient) to materials properties (i.e. Young's modulus, Poisson ratio, shear modulus). Other testing performed on the test artifact can include electrical resistivity, thermal conductivity, ultrasonic response, and aging related tests. This non-destructive testing approach enables repeat evaluation of the same part in varying environments (i.e., at differing temperatures and/or pressures, surface modifications or surface coatings) to determine changes in the material properties and mechanical response, for example after repeated heat treatments or surface modifications. The flexural cantilever design of the test artifacts simultaneously enables non-destructive determination of bulk transport properties for metals of electrical resistivity, and indirectly, via calculation, also the thermal conductivity. Correlations between electrical resistivity can also be used to estimate defect density and grain size. Measurements of electrical resistivity can be performed by contacting with two pairs of electrodes on opposite sides of one or multiple flexures, in series or in parallel. Each of the two electrode pairs include a current supply line and a voltage measurement line to perform a 4-wire resistance measurement. Simplifications afforded by the thin, high aspect ratio geometry of the flexures of the test artifact allow for simple calculation of resistivity.

In another embodiment of the present invention, a test artifact can be used in an automated test sequence and be done with quick turn-around. The test artifact can also be modified and/or tailored for specific needs.

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A test artifact comprising:
   a support frame;
   a first cantilever section disposed on the support frame, the first cantilever section comprising a first cantilever and a second cantilever;
   a second cantilever section disposed on the support frame and substantially parallel to the first cantilever section, the second cantilever section comprising a third cantilever and a fourth cantilever;
   a support beam connecting the first cantilever section to the second cantilever section;
   an end portion connecting the second cantilever to the third cantilever and disposed on ends of the second and third cantilevers opposite the support beam;
   a protrusion disposed on the end portion; and
   a mounting portion attached to the support frame.

2. The test artifact of claim 1 wherein the mounting portion comprises one or more fixturing stubs.

3. The test artifact of claim 1, wherein the mounting portion comprises an opening.

4. The test artifact of claim 1, wherein each of the cantilevers are substantially the same thickness.

5. The test artifact of claim 1, wherein each of the cantilevers vary in thickness.

6. The test artifact of claim 5, wherein a thickness of each respective cantilever is substantially constant and the thickness varies from one of the cantilevers to another of the cantilevers.

7. The test artifact of claim 1, wherein each of the cantilevers vary in height along a length of a corresponding cantilever.

8. The test artifact of claim 7, wherein a height of each cantilever is greater at an end adjacent to the support beam than at a corresponding end adjacent to the end portion.

9. The test artifact of claim 1, further comprising a center portion disposed between the first cantilever section and the second cantilever section.

10. The test artifact of claim 9, wherein the center portion extends from the end portion.

11. The test artifact of claim 1, wherein the mounting portion is substantially perpendicular to each of the cantilevers.

12. The test artifact of claim 1, wherein the mounting portion is substantially parallel to each of the cantilevers.

13. The test artifact of claim 1, further comprising a third cantilever section and a fourth cantilever section.

14. The test artifact of claim 13, wherein the third cantilever section is adjacent to the first cantilever section and the fourth cantilever section is adjacent to the second cantilever section.

15. The test artifact of claim 1, wherein the support frame is c-shaped.

16. The test artifact of claim 1, wherein the artifact is one continuous part with no assembly.

17. A test artifact comprising:
   a support frame;
   a first cantilever section attached to the support frame, the first cantilever section comprising at least one first support cantilever and at least one first load cantilever;
   a second cantilever section attached to the support frame and substantially parallel to the first cantilever section, the second cantilever section comprising at least one second support cantilever and at least one second load cantilever;
   a support beam attached to the at least one first support cantilever, the at least one first load cantilever, the at least one second support cantilever, and the at least one second load cantilever;
   a load portion attached to the at least one first load cantilever and the at least one second load cantilever at ends of the corresponding load cantilevers opposite the support beam;
   a protrusion attached to the load portion; and
   a mounting portion attached to the support frame.

18. The test artifact of claim 17, wherein the at least one first support cantilever includes two first support cantilevers; and the at least one second support cantilever includes two second support cantilevers.

19. The test artifact of claim 17, wherein the at least one first load cantilever includes two first load cantilevers; the at least one second load cantilever includes two second load cantilevers.

20. The test artifact of claim 17, wherein
   the at least one first support cantilever includes two first support cantilevers;
   the at least one first load cantilever includes two first load cantilevers;
   the at least one second support cantilever includes two second support cantilevers; and
   the at least one second load cantilever includes two second load cantilevers.

* * * * *